United States Patent [19]
Hirschberg

[11] Patent Number: 5,387,234
[45] Date of Patent: Feb. 7, 1995

[54] MEDICAL ELECTRODE DEVICE

[75] Inventor: Jakub Hirschberg, Taeby, Sweden

[73] Assignee: Siemens-Elema AB, Solna, Sweden

[21] Appl. No.: 63,569

[22] Filed: May 19, 1993

[30] Foreign Application Priority Data

May 21, 1992 [SE] Sweden .................... 9201559

[51] Int. Cl.⁶ ............................................ A61N 1/05
[52] U.S. Cl. .................................................. 607/129
[58] Field of Search ........................ 607/115–119, 607/122, 125–132; 128/642

[56] References Cited

U.S. PATENT DOCUMENTS

| | | |
|---|---|---|
| 4,567,900 | 2/1986 | Moore . |
| 4,628,937 | 12/1986 | Hess et al. ............... 128/642 |
| 4,763,660 | 8/1988 | Kroll et al. . |
| 4,817,634 | 4/1989 | Holleman et al. . |
| 4,938,231 | 7/1990 | Milijasevic et al. . |
| 5,016,645 | 5/1991 | Williams et al. . |
| 5,042,463 | 8/1991 | Lehholm .................. 607/129 |
| 5,063,932 | 11/1991 | Dahl et al. . |
| 5,105,826 | 4/1992 | Smits et al. . |
| 5,190,052 | 3/1993 | Schroeppel ............... 128/642 |

Primary Examiner—Lee S. Cohen
Assistant Examiner—Marianne Parker
Attorney, Agent, or Firm—Hill, Steadman & Simpson

[57] ABSTRACT

A medical electrode device has a flat, flexible and electrically insulating electrode carrier, on which at least one electrode conductor is arranged in a predetermined pattern, the conductor being partially exposed to define an electrode surface through which electrical energy is delivered in vivo to tissue adjacent the surface. The electrode carrier insulates the passive side of the electrode from surrounding tissue. The electrode surface defined by the conductor has a relatively broad extent, such as for defibrillating a heart. The electrode carrier has at least one opening therein extending through the predetermined pattern of the electrode conductor, so as to reduce the insulative effect and to increase the flexibility and resilience of the electrode carrier.

11 Claims, 1 Drawing Sheet

FIG 1
FIG 2
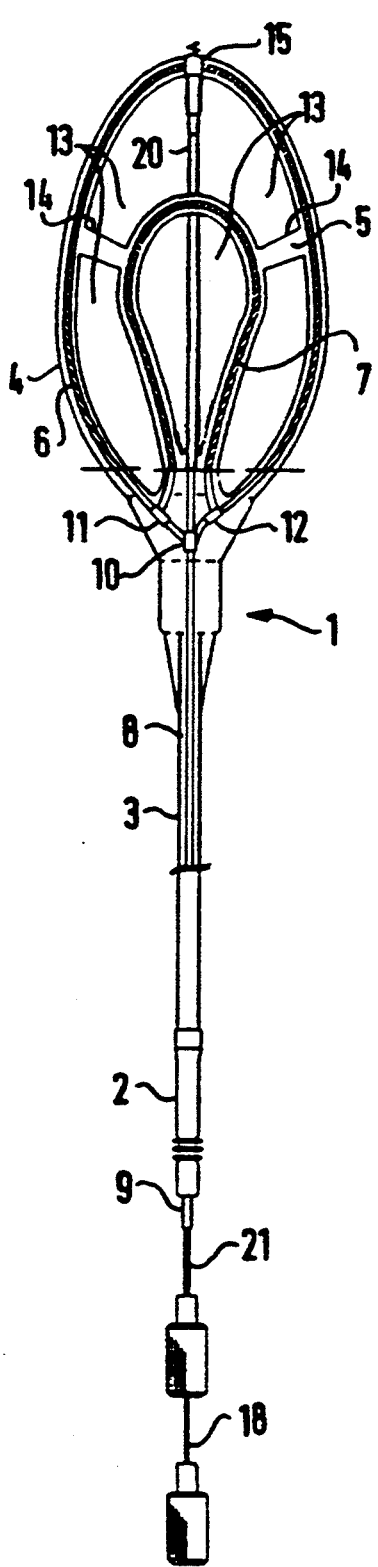
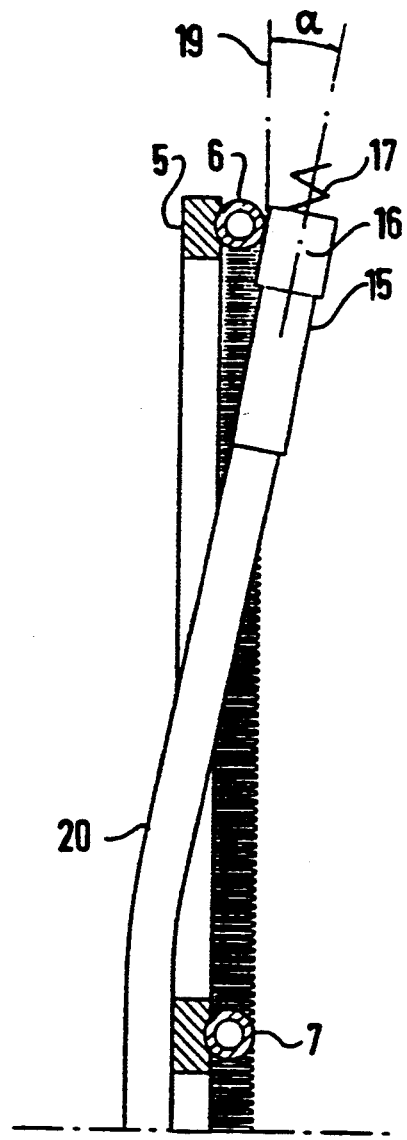

MEDICAL ELECTRODE DEVICE

BACKGROUND OF THE INVENTION

1. Field of the Invention

The present invention is directed to an implantable electrode device, of the type intended for connection to a medical apparatus for delivering electrical energy, such as electrical pulses, to living tissue.

2. Description of the Prior Art

Implantable electrode devices are generally known in the art for connection to a medical apparatus to deliver electrical impulses in vivo to tissue. Such known devices include an electrode catheter which contains a lead, one end of which is equipped with a connection contact (jack) for inserting the lead into a pulse generator, the other end of the catheter and lead being connected to a flat, flexible electrode carrier consisting of electrically insulating material, on which at least one electrode conductor is arranged in a predetermined pattern, the conductor being electrically conducted to the lead. A portion of the conductor is exposed to form an active electrode surface.

Such an electrode device is disclosed in U.S. Pat. No. 4,817,634. In this known electrode device, the insulating electrode carrier has a groove therein which follows a predetermined pattern in which an electrode conductor is placed. The electrode conductor is coiled around an insulating core, and is coupled to a contact clamp for electrically coupling an electrode lead thereto, contained in an electrode catheter. The electrode device is designed to be sutured to the heart of a patient in order to transmit defibrillation pulses to the heart from an implanted defibrillator.

During implantation of this known electrode device in a patient, the device is placed so that it surrounds a large portion of the heart, thereby substantially electrically insulating the heart from its surrounding tissue. As a result, any external defibrillation pulse subsequently delivered to the patient could be wholly or partially ineffective, because the insulating electrode carrier would prevent such externally-applied electrical impulses from reaching the heart. In addition, this known electrode device presents an obstacle to any subsequent heart surgery, for example, for removal of damaged heart tissue.

Another known electrode device is disclosed in U.S. Pat. No. 4,567,900 wherein the electrode is formed by a resilient conductor curved in such a manner as to exhibit a ring-shaped electrode contour. Thin, flexible, conductor strips are arranged in a grid pattern within the ring-shaped contour to form the electrode surface. The conductor can be compressed into a narrow, elongated form in which it can be placed inside an introducer catheter and thereby advanced to the heart. The electrode is completely uninsulated and is designed for loose placement between the pericardium and the epicardium. If the electrode were placed at any other location, the uninsulated electrode could damage adjacent tissue. There is no discussion in this patent as to how the electrode would be prevented from shifting position before it becomes embedded in cardiac tissue by tissue ingrowth.

SUMMARY OF THE INVENTION

It is an object of the present invention to provide an electrode device of the type having an active electrode surface formed by at least one conductor mounted in an electrode carrier for delivering electrical energy to a relatively large expanse of heart tissue, but which does not electrically insulate the heart from surrounding tissue, and which leaves as much heart tissue as possible exposed and accessible for subsequent external measures.

It is a further object of the present invention to provide such an electrode device which does not change position after implantation.

The above object is achieved in accordance with the principles of the present invention in an electrode device having an electrode carrier with at least one opening therein in a surface thereof located at the side of the electrode at which the active electrode surface is present.

Providing the electrode carrier with one or more openings, through which the electrode conductor does not pass, results in an electrode device which is more flexible than the known electrode described in U.S. Pat. No. 4,817,634 and which can be advanced to the heart, coiled inside an introducer in a manner similar to that described in U.S. Pat. No. 4,567,900. As a result of the one or more openings, the electrode carrier is located substantially only along the predetermined path of the conductor, so that electrical insulation of the heart with respect to externally-applied defibrillation pulses is minimized, and access to heart tissue is simultaneously maximized without a reduction in the effective area of the electrode. The openings also make the electrode more flexible, so that it does not impede the heart's movements to the extent as does a conventional electrode carrier without openings. The ability of the carrier to conform to the heart's movements also reduces the risk of displacement of the position of the electrode carrier on the heart.

The electrode catheter can be provided with a channel extending therethrough along its longitudinal axis, with the electrode catheter being mechanically connected at a peripheral region of the electrode carrier. A tubular element can be attached to the electrode carrier so that it constitutes an extension of the electrode catheter, the tubular element being closed at its free end with a stopper. A stylet is introducible into the electrode catheter and into the tubular element up to the stopper.

The stylet facilitates manipulation of the electrode device during introduction into the body of the patient. With the aid of the stylet, control of placement of the electrode against the tissue is improved. In addition, the outer contour of the electrode carrier can be changed by manipulation of the stylet during introduction. Because the tubular element is elastic and the stopper impedes the stylet at the free end of the tubular element, the electrode carrier can be extended when the stylet is pressed against the stopper. As noted above, due to the openings in the electrode carrier the flexibility of the electrode carrier is increased, thereby reducing the force required to extend the electrode carrier and enabling the extended electrode carrier to become embedded in tissue without damaging the tissue. When the stylet is withdrawn, the surrounding tissue maintains the force required to keep the electrode carrier extended. The stylet and the stopper can also be devised so that the stylet, at a given position, is releasably latched to the stopper, thereby compressing the electrode carrier when the stylet is withdrawn. In the same manner as with the extension of the electrode carrier, the compressed electrode carrier can then be attached to tissue, with the stylet thereafter being removed. The contour of the electrode carrier can thus easily be adapted, for example, to the contour of the heart in such a manner that electrical pulses supplied by the electrode have the greatest possible effect.

The tubular element may be formed by a further, coiled electrode conductor which is electrically connected to the electrode lead in the catheter, so that the active electrode surface is increased without further limiting access to the heart or further increasing the insulating effect of the electrode carrier on the heart. Preferably, the conductor contained in the electrode carrier and the conductor forming the tubular element each consist of a single conductor wire, so as to result in fewer coupling points and thus resulting in a simpler fabrication of the overall electrode device.

Alternately, the tubular element may consist of insulating material as an extension of the electrode catheter.

In a further embodiment of the electrode device according to the invention, the free end of the tubular element contains a movable, fixing device for attaching the electrode device to surrounding tissue, the fixing device being controllable with the stylet. The fixing device enables the electrode to be affixed more effectively at a desired position on the heart, making surgery less traumatic, because the fixing is controlled by a remote procedure. Preferably the stylet is a double stylet, one stylet of which controls the fixing device and the other stylet controlling the change in the contour of the electrode.

For coupling the electrode conductor and the lead contained in the catheter, it is preferable if the electrode conductor is coiled and thereby permitting the coupling to be achieved by coiling the electrode conductor and the lead around each other or intertwining the electrode conductor with the lead. The number of components is thereby reduced, since no special contact elements, such as crimping elements, are necessary. If a plurality of electrode conductors are used to form the predetermined pattern on the electrode carrier, the pattern in which the conductors are arranged can be varied to a greater degree than if fixed contact elements are used for coupling the conductors. The electrode carrier can then retain its flexibility in the contact area.

DESCRIPTION OF THE DRAWINGS

FIG. 1 is a plan view of an embodiment of an electrode device constructed in accordance with the principles of the present invention.

FIG. 2 is an enlarged side view, partly in section, of a fixing element carried on the electrode device on FIG. 1.

DESCRIPTION OF THE PREFERRED EMBODIMENTS

The electrode device 1 shown in FIG. 1 generally includes three main components: a connection contact (jack) 2 for coupling the electrode device 1 to a stimulation pulse generator (not shown) such as a defibrillator, an electrode catheter 3, and an electrode 4 having an active electrode surface through which a electrical energy, such as a stimulation pulse generated by the defibrillator, is delivered to a heart. The electrode 4 is formed by a flat, electrically insulating electrode carrier 5, a first coiled electrode conductor 6 arranged at the periphery of the electrode carrier 5, and a second coiled electrode conductor 7 arranged in a simple loop inside the first electrode conductor 6, and a third electrode conductor 20 attached to the electrode carrier 5 such that it constitutes an extension of an electrode lead 8 which runs inside the length of the electrode catheter 3 from a terminal 9 at the connection contact 2. The electrode lead 8 is coiled and thereby forms a channel in the center of the electrode catheter 3 running the length of the catheter 3.

The electrode conductors 6 and 7 are partially exposed from the electrode carrier 5 and thus define an electrode surface, which may be augmented by the electrode conductor 20.

The first electrode conductor 6 is mechanically and electrically coupled to the electrode lead 8 in a contact area 10 by means of the flights of those respective coiled conductors being intertwined. In a corresponding manner the second electrode conductor 7 is mechanically and electrically coupled to the first electrode conductor 6 at the ends 11 and 12 of the loops.

The electrode conductors 6 and 7 and the electrode lead 8 preferably consist of compound wire having a low-resistance core and a biocompatible sleeve. The core is preferably made of copper, a copper compound, silver or a silver alloy, with the sleeve consisting of MP35N alloy (an alloy made of nickel, cobalt, chromium and molybdenum), titanium, a titanium alloy, platinum or a platinum alloy. The use of a low-resistance core provides better and more uniform distribution of current over the conductors 6 and 7.

The electrode carrier 5 has a plurality of openings 13 between the paths of the conductors 6, 7 and 20. The openings 13 serve a number of purposes. First, they make the electrode 4 more flexible than a conventional electrode without openings, so that the electrode 4 can be easily coiled in order to advance it to the heart through an introducer catheter in the manner described in U.S. Pat. No. 4,567,900. Moreover, the insulative effect of the electrode carrier 4 on the heart, when the electrode 4 is applied to the heart, is reduced without any reduction in the effective area of the active electrode. This permits an electrical pulse from, for example, an extracorporeal defibrillator, to pass through the openings 13 in the electrode carrier 4 to heart tissue, and additionally exposes most of the heart for access in the event of subsequent surgery, for example, for removal of damaged heart tissue. The various electrode loops are held together with bridges 14 consisting of insulating material, which also contribute to maintaining the planar shape of the electrode 4.

For attaching the electrode 4 to the heart, the electrode device 1 includes a fixing device 15 at the free end of the third conductor 20. As shown in FIG. 2, the fixing device 15 includes a sleeve 16 and a helix 17 having a pointed tip. The helix 17 is rotated in and out of the sleeve 16 using a stylet 18, which temporarily mechanically engages the helix 17, or a mounting element for the helix 17. The stylet 18 is introduced from the connection contact 2 and runs in the channel in the electrode catheter 3 (i.e., inside the coiled conductor 8) and the inside the third conductor 20 to the fixing device 15. The direction of advancement of the helix 17 follows a line which forms a small angle α with the plane 19 of the electrode surface. As a result of the angle α, the helix 17 emerges from the plane 19 of the electrode surface when screwed out of the sleeve 16 so that the helix 17 can seat itself, for example, in the pericardium around the heart. Since only the pericardium is utilized for attaching the electrode to the heart, there is no damage to the epicardium. Additionally, the pericardium remains generally intact, so that its function of protecting the heart is uncompromised.

If the implantation site initially selected for the electrode 4 proves to be unsuitable, the helix 17 can simply be retracted back into the sleeve 16 using the stylet 18. The electrode 4 can then be moved to some other location on the heart and attached.

The electrode device disclosed herein can alternatively be applied subcutaneously. For such a subcutaneous implantation, the angle α is preferably increased, and a longer helix 17 is used, depending on the sensitivity of the tissue which will be penetrated by the helix 17. The helix 17 may alternatively be itself angled, so that it screws out of the back (passive side) of the electrode 4, or straight outwardly along the extension of the electrode catheter 3. This may be preferable if less sensitive tissue is near the tissue to be stimulated. In the above example, the helix 17 is disposed at the distal end of the electrode 4 (i.e., distal relative to the end of the catheter 3), but could be located anywhere along the length of the electrode 4.

Placement of the electrode 4 against the heart is additionally facilitated by manipulation of the stylet 18. The electrode 4 can be moved, and its contour changed, by means of the stylet 18 or, more preferably, by providing a double stylet, with the stylet 18 being used exclusively for operating the fixing device 15, and an additional stylet 21 of the double stylet being used to alter the contour of the electrode 4. The alteration in contour is accomplished by the second stylet 21 pressing against a stopper at the end of the third electrode conductor 20 so that the electrode carrier 5 is stretched. The stopper may, for example, consist of the fixing device 15. In its stretched state, the electrode carrier 5 can then be affixed to the heart, and the double stylet can thereafter be removed. Although in principle one stylet, such as the stylet 18, can suffice for controlling both the fixing device 15 and changing the contour of the electrode 4, control over the respective functions is improved if a double stylet is used.

The electrode carrier 5 can also be compressed if the stylet and stopper are devised so that the stylet, such as the stylet 21, in a given position, is latched to a location near the distal end of the electrode 4. Retracting the stylet the compresses the electrode carrier 5, enabling it to be affixed to the heart in a compressed state. The latching is releasable, so that the stylet can then be withdrawn completely.

The objective of altering the contour of the electrode 4 during implantation is to increase the ability of the electrode 4 to adapt to the contour of an individual heart, and thereby to optimize the effect of the electrical pulses, since the contour of the electrode surface governs, to a certain extent, the path which the pulses take through the heart tissue.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable electrode device adapted for connection to a medical apparatus for delivering electrical energy in vivo to tissue, said electrode device comprising:
   a catheter containing an electrical conductor, each of said catheter and electrical conductor having a first end and a second end and said catheter and electrical conductor having a connection contact disposed at said first ends; and
   a flat, flexible electrode carrier consisting of electrically insulating material disposed at said second ends of said catheter and said electrical conductor, said electrode carrier containing at least one electrode conductor electrically connected to said electrical conductor and arranged in a predetermined path on said electrode carrier to define an electrode surface, said electrode carrier having an opening at least partially surrounded by said predetermined path.

2. An electrode device as claimed in claim 1 wherein said catheter has a channel extending therethrough, and wherein said catheter is mechanically attached at a periphery of said electrode carrier, and said electrode device further comprising a tubular element mechanically attached to said electrode carrier and forming an extension of said catheter, said tubular element having a free end closed with a stopper, and said electrode device further comprising stylet means introducible into said channel in said catheter and into said tubular element for temporarily mechanically engaging said stopper.

3. An electrode device as claimed in claim 2 wherein said tubular element comprises a coiled electrode conductor electrically connected to said electrical conductor.

4. An electrode device as claimed in claim 3 wherein said coiled electrode conductor and said electrical conductor each consist of a single conductor wire.

5. An electrode device as claimed in claim 2 wherein said tubular element consists of an extension of said catheter consisting of insulating material.

6. An electrode device as claimed in claim 2 wherein said tubular element has a free end and wherein said electrode device further comprises a movable fixing element temporarily engageable with said stylet means for operating said fixing element to affix said electrode device to tissue.

7. An electrode device as claimed in claim 6 wherein said stylet means comprises a double stylet system including first and second stylets, said first stylet temporarily mechanically engaging said fixing element and said second stylet temporarily mechanically engaging said stopper.

8. An electrode device as claimed in claim 6 wherein said fixing element comprises said stopper.

9. An implantable electrode device adapted for connection to a medical apparatus for delivering electrical energy in vivo to tissue, said electrode device comprising:
   a catheter containing an electrical conductor, each of said catheter and electrode lead having a first end and a second end and said catheter and electrical conductor having a connection contact disposed at said first ends; and
   a flat, flexible electrode carrier consisting of electrically insulating material disposed at said second ends of said catheter and said electrical conductor, said electrode carrier containing at least one electrode conductor electrically connected to said electrical conductor and arranged in a predetermined path forming a closed loop on said electrode carrier to define an electrode surface, said electrode carrier having an opening surrounded by said closed loop predetermined path.

10. An implantable electrode device adapted for connection to a medical apparatus for delivering electrical energy in vivo to tissue, said electrode device comprising:
- a catheter containing an electrical conductor, each of said catheter and electrical conductor having a first end and a second end and said catheter and said electrical conductor having a connection contact disposed at said first ends; and
- a flat, flexible electrode carrier consisting of electrically insulating material disposed at said second ends of said catheter and said electrical conductor, said electrode carrier containing two electrode conductors electrically connected to said electrical conductor and respectively arranged in two closed loop paths on said electrode carrier to define an electrode surface, said electrode carrier having an opening surrounded by said two closed loop paths.

11. An implantable electrode device as claimed in claim 10 further comprising at least one bridge element consisting of said electrically insulating material extending between said first and second closed loops across said opening.

* * * * *